(12) United States Patent  
Takahashi et al.

(10) Patent No.: US 9,936,568 B2  
(45) Date of Patent: Apr. 3, 2018

(54) X-RAY GENERATOR, X-RAY IMAGING APPARATUS INCLUDING THE X-RAY GENERATOR, AND METHOD OF CONTROLLING THE X-RAY GENERATOR

(71) Applicant: SAMSUNG ELECTRONICS CO., LTD., Suwon-si, Gyeonggi-do (KR)

(72) Inventors: Jun Takahashi, Suwon-si (KR); Keun Su Chang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 271 days.

(21) Appl. No.: 14/450,759

(22) Filed: Aug. 4, 2014

(65) Prior Publication Data

US 2015/0055750 A1 Feb. 26, 2015

(30) Foreign Application Priority Data

Aug. 22, 2013 (KR) ........................ 10-2013-0099678

(51) Int. Cl.
*H05G 1/10* (2006.01)
*H05G 1/48* (2006.01)
(Continued)

(52) U.S. Cl.
CPC ............... *H05G 1/10* (2013.01); *G01N 23/04* (2013.01); *H01J 35/025* (2013.01); *H05G 1/48* (2013.01)

(58) Field of Classification Search
CPC G01N 23/04; H05G 1/10; H05G 1/32; H05G 1/12; H05G 2/00; H05G 1/56; H05G 1/58; H05G 1/48
See application file for complete search history.

(56) References Cited

U.S. PATENT DOCUMENTS 4,181,857 A * 1/1980 Miyoshi ................... H05G 1/24  
378/103  
4,238,683 A * 12/1980 Baumann ................. H05G 1/14  
324/119  
(Continued)

FOREIGN PATENT DOCUMENTS

FR 2238312 2/1975  
JP 11-74096 3/1999  
(Continued)

OTHER PUBLICATIONS

Extended European Search Report dated Dec. 23, 2014 from European Patent Application No. 14180421.1, 6 pages.

(Continued)

*Primary Examiner* — Hoon Song  
(74) *Attorney, Agent, or Firm* — Staas & Halsey LLP

(57) ABSTRACT

An X-ray generator is capable of reducing invalid exposure caused due to wave tails, which do not contribute to the quality of an X-ray image, by preventing the wave tails from being supplied to an X-ray tube. An X-ray imaging apparatus includes the X-ray generator and a method of reducing the invalid exposure is implemented using the X-ray generator. The X-ray generator includes an X-ray tube to generate X-rays, and a high-voltage generator to supply a voltage having a pulse waveform to the X-ray tube. The high-voltage generator includes a high-voltage tank to generate a high voltage, a switch connected to an output terminal of the high-voltage tank and turned on or off, and a resistor located outside the high-voltage tank to receive a wave tail voltage having the pulse waveform and to consume power generated due to wave tails.

26 Claims, 17 Drawing Sheets

(51) Int. Cl.
*G01N 23/04* (2018.01)
*H01J 35/02* (2006.01)

(56) References Cited

U.S. PATENT DOCUMENTS

| | | | |
|---|---|---|---|
| 5,056,125 A * | 10/1991 | Beland | H05G 1/08 378/101 |
| 5,339,349 A | 8/1994 | Xeno | |
| 2006/0210013 A1 | 9/2006 | Kasuya | |

FOREIGN PATENT DOCUMENTS

| JP | 2001-284097 | 10/2001 |
|---|---|---|
| JP | 2007-95530 | 4/2007 |
| JP | 2012-120653 | 6/2012 |

OTHER PUBLICATIONS

Korean Office Action dated Nov. 28, 2014 from Korean Patent Application No. 10-2013-0099678, 10 pages.
European Office Action dated Dec. 6, 2016 from European Patent Application No. 14 180 421.1, 46 pages.

* cited by examiner

X-RAY GENERATOR, X-RAY IMAGING APPARATUS INCLUDING THE X-RAY GENERATOR, AND METHOD OF CONTROLLING THE X-RAY GENERATOR

CROSS-REFERENCE TO RELATED APPLICATIONS

This application claims the benefit of Korean Patent Application No. 10-2013-0099678, filed on Aug. 22, 2013 in the Korean Intellectual Property Office, the disclosure of which is incorporated herein by reference.

BACKGROUND

1. Field

Embodiments disclosed herein relate to an X-ray generator to generate and radiate X-rays to an object, an X-ray imaging apparatus including the X-ray generator, and a method of controlling the X-ray generator.

2. Description of the Related Art

Generally, an X-ray imaging apparatus radiates X-rays to an object and acquires an image of the inside of the object using the X-rays having passed through the object. Since an object has different X-ray transmittances depending on characteristics of materials of the object, the internal structure of the object may be imaged by detecting the intensity or strength of X-rays having passed through the object.

The X-ray imaging apparatus may include an X-ray generator to generate and radiate X-rays to an object, and the X-ray generator may include an X-ray tube to generate X-rays due to collision of electrons between an anode and cathode, and a high-voltage generator to apply a high voltage to the anode and cathode of the X-ray tube.

The high-voltage generator and the X-ray tube may be connected through high-voltage cables, and wave tails may be generated due to stray capacitance of the high-voltage cables, thereby increasing exposure of or to the object.

SUMMARY

Therefore, it is an aspect of the disclosure to provide an X-ray generator capable of reducing invalid exposure caused due to wave tails, which do not contribute to the quality of an X-ray image, by preventing the wave tails from being supplied to an X-ray tube. Further, an X-ray imaging apparatus including the X-ray generator capable of reducing invalid exposure caused due to wave tails, and a method of controlling the X-ray generator to reduce invalid exposure caused due to wave tails are provided.

Additional aspects of the disclosure will be set forth in part in the description which follows and, in part, will be apparent from the description, or may be learned by practice of the disclosure.

In accordance with an aspect of the disclosure, an X-ray generator may include an X-ray tube to generate X-rays, and a high-voltage generator to supply a voltage having a pulse waveform to the X-ray tube. The high-voltage generator may include a high-voltage tank to generate a high voltage, a switch connected to an output terminal of the high-voltage tank and which is turned on or off, and a resistor located outside the high-voltage tank to receive a wave tail voltage having the pulse waveform and applied according to an on or off status of the switch and to consume power generated due to wave tails.

The high-voltage tank may include a step-up transformer to boost power supplied from a power supply to a high voltage, and a rectifier to rectify the boosted power.

The high-voltage generator may further include a step-down transformer to drop the wave tail voltage applied to the resistor.

The switch and the step-down transformer may be located in the high-voltage tank.

The step-down transformer may have a primary coil connected to the output terminal of the high-voltage tank and a secondary coil connected to the resistor.

The resistor may be located in an insulated sub tank.

The high-voltage generator may supply a voltage to the X-ray tube according to a preset pulse rate and a pulse width.

The X-ray generator may further include a controller to control an on or off position, status, or state of the switch.

The controller may synchronize a wave tail generation point with an on point of the switch, and the resistor may receive the wave tail voltage applied when the switch is turned on.

The controller may synchronize a wave tail extinction point or a next pulse rising point with an off point of the switch.

The controller may determine the on point and the off point of the switch based on the pulse rate and the pulse width.

The high-voltage generator may further include a converter to convert alternating current (AC) power supplied from the power supply, into direct current (DC) power, and an inverter to convert the converted DC power into high-frequency AC power.

The X-ray generator may further include a cooler to cool the inverter, and the resistor may be located in a cooling region of the cooler to be cooled together with the inverter.

The high-voltage tank may include an anode output terminal connected to an anode of the X-ray tube, and a cathode output terminal connected to a cathode of the X-ray tube, and two terminals of the switch may be respectively connected to the anode output terminal and the cathode output terminal.

The X-ray generator may further include a forward diode located between the output terminal of the high-voltage tank and the step-down transformer.

In accordance with an aspect of the disclosure, an X-ray imaging apparatus may include an X-ray generator to generate X-rays; and an X-ray detector to detect the X-rays generated by the X-ray generator, wherein the X-ray generator comprises an X-ray tube to generate the X-rays; and a high-voltage generator to supply a voltage to the X-ray tube, wherein the high-voltage generator comprises a high-voltage tank to generate a high voltage a switch connected to an output terminal of the high-voltage tank; and a resistor located outside the high-voltage tank to receive a wave tail voltage according to an on or off status of the switch.

For example, the high-voltage generator included in the X-ray imaging apparatus may further include a step-down transformer to drop the wave tail voltage. The switch and the step-down transformer may be located in the high-voltage tank. The high-voltage generator may further include a forward diode located between the output terminal of the high-voltage tank and the step-down transformer.

The resistor may be located in an insulated sub tank.

For example, the high-voltage generator included in the X-ray imaging apparatus may further include a converter to convert alternating current (AC) power supplied from a power supply, into direct current (DC) power, an inverter to convert the converted DC power into high-frequency AC power, and a cooler to cool the inverter and the resistor.

The X-ray generator of the X-ray imaging apparatus may further include a controller to control a status of the switch. The controller may synchronize a wave tail generation point with an on point of the switch, and the resistor may receive the wave tail voltage when the switch is turned on. The controller may synchronize a wave tail extinction point or a next pulse rising point with an off point of the switch. The controller may control a status of the switch, the high-voltage generator may supply a voltage to the X-ray tube according to a preset pulse rate and a pulse width, and the controller may determine the on point and the off point of the switch based on the preset pulse rate and the pulse width.

In accordance with an aspect of the disclosure, a method of controlling an X-ray generator including an X-ray tube to generate X-rays, and a high-voltage generator to supply a voltage having a pulse waveform to the X-ray tube, may include determining a wave tail generation point of the pulse waveform, synchronizing an on point of a switch connected to an output terminal of a high-voltage tank, with the wave tail generation point, and, if or when the switch is turned on, applying a wave tail voltage to a resistor located outside the high-voltage tank, and consuming power generated due to wave tails using the resistor.

The method may further include synchronizing a wave tail extinction point or a next pulse rising point with an off point of the switch.

The method may further include, if or when the switch is turned on, dropping the wave tail voltage using a step-down transformer located in the high-voltage tank, and applying the dropped wave tail voltage to the resistor.

The resistor may be located in an insulated sub tank.

The method may further include, if or when the switch is turned on, blocking backward current generated from a primary coil of the step-down transformer from being transferred toward the X-ray tube, using a forward diode.

The method may further include converting alternating current (AC) power supplied from a power supply, into direct current (DC) power, converting, using an inverter disposed in the high-voltage generator, the converted DC power into high-frequency AC power, and cooling the inverter and the resistor using a same cooler.

In accordance with an aspect of the disclosure, an X-ray generator may include an X-ray tube to generate X-rays, and a high-voltage generator to supply a voltage to the X-ray tube, and a wave tail blocking circuit connected in parallel to an output terminal of the high voltage generator, to prevent wave tails from being supplied to the X-ray tube. The wave tail blocking circuit may include a switch which is used to control a flow of charges accumulated as stray capacitance into the wave tail blocking circuit based on an output of the voltage supplied to the X-ray tube, and a resistor which receives an application of wave tail voltage to discharge the flow of charges accumulated as stray capacitance. The switch may be disposed inside a high voltage tank and the resistor may be disposed outside of the high voltage tank.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
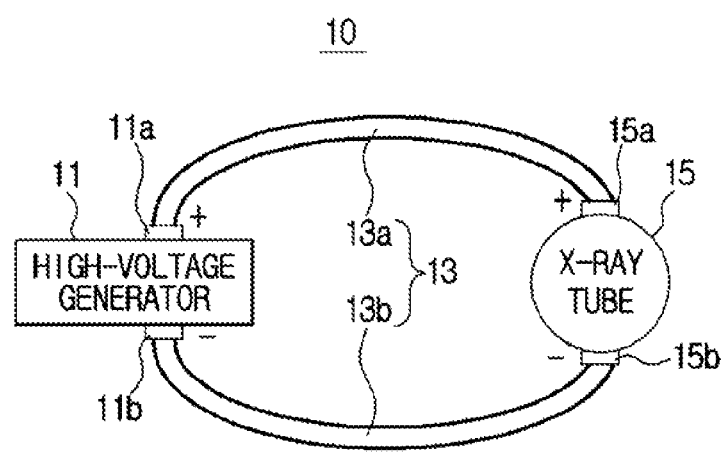
FIG. 1 is a schematic view showing connection between a high-voltage generator and an X-ray tube of an X-ray generator.

Reference will now be made in detail to the embodiments of the disclosure, examples of which are illustrated in the accompanying drawings, wherein like reference numerals refer to like elements throughout.

Figure 2:
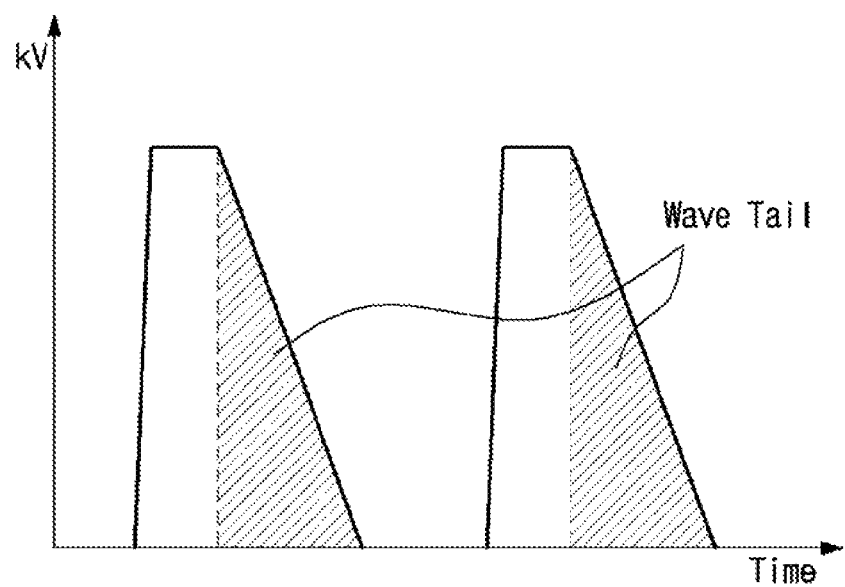
FIG. 2 is a graph showing the waveform of a voltage supplied to the X-ray tube.

FIG. 1 is a schematic view showing A connection between a high-voltage generator 11 and an X-ray tube 15 of an X-ray generator 10, and FIG. 2 is a graph showing the waveform of a voltage supplied to the X-ray tube 15.

Referring to FIG. 1, the X-ray generator 10 may include the high-voltage generator 11 to generate and supply a high voltage to the X-ray tube 15, and the X-ray tube 15 to generate and radiate X-rays when the high voltage is applied to two terminals thereof. The high-voltage generator 11 and the X-ray tube 15 may be connected through high-voltage cables 13 including an anode cable 13a and a cathode cable 13b.

Specifically, an anode output terminal 11a of the high-voltage generator 11 may be connected to an anode input terminal 15a of the X-ray tube 15 through the anode cable 13a, and a cathode output terminal 11b of the high-voltage generator 11 may be connected to a cathode input terminal 15b of the X-ray tube 15 through the cathode cable 13b.

The voltage applied to the X-ray tube 15 may have a pulse waveform. In this case, most ideally, a falling time of the waveform may be 0 to reduce invalid exposure of or to an object. However, actually, due to stray capacitance of the high-voltage cables 13, as illustrated in FIG. 2, the falling time is increased and thus wave tails are generated. By way of a non-limiting example, due to stray capacitance of the high-voltage cables 13 the falling time may be increased up to about 20 ms and wave tails are generated.

The wave tails of FIG. 2 are generated when charges accumulated as the stray capacitance of the high-voltage cables 13 are gradually discharged. If charges forming wave tails, i.e., charges accumulated as stray capacitance and discharged gradually, are supplied to the X-ray tube 15, invalid exposure, which does not contribute to the quality of an X-ray image, is generated. In addition, when the wave tails are long, a rapid pulse rate may not be easily achieved.

Therefore, according to an embodiment of the disclosure, an X-ray generator and an X-ray imaging apparatus including the same may include a wave tail blocking circuit to block charges forming wave tails from being supplied to an X-ray tube.

Figure 3:
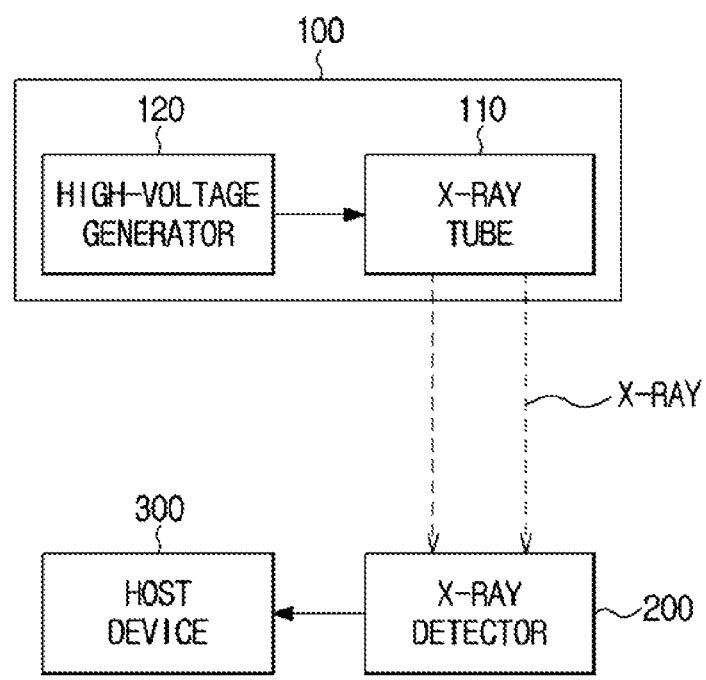
FIG. 3 is a control block diagram of an X-ray generator and an X-ray imaging apparatus including the same, according to an embodiment of the disclosure.
Figure 12:
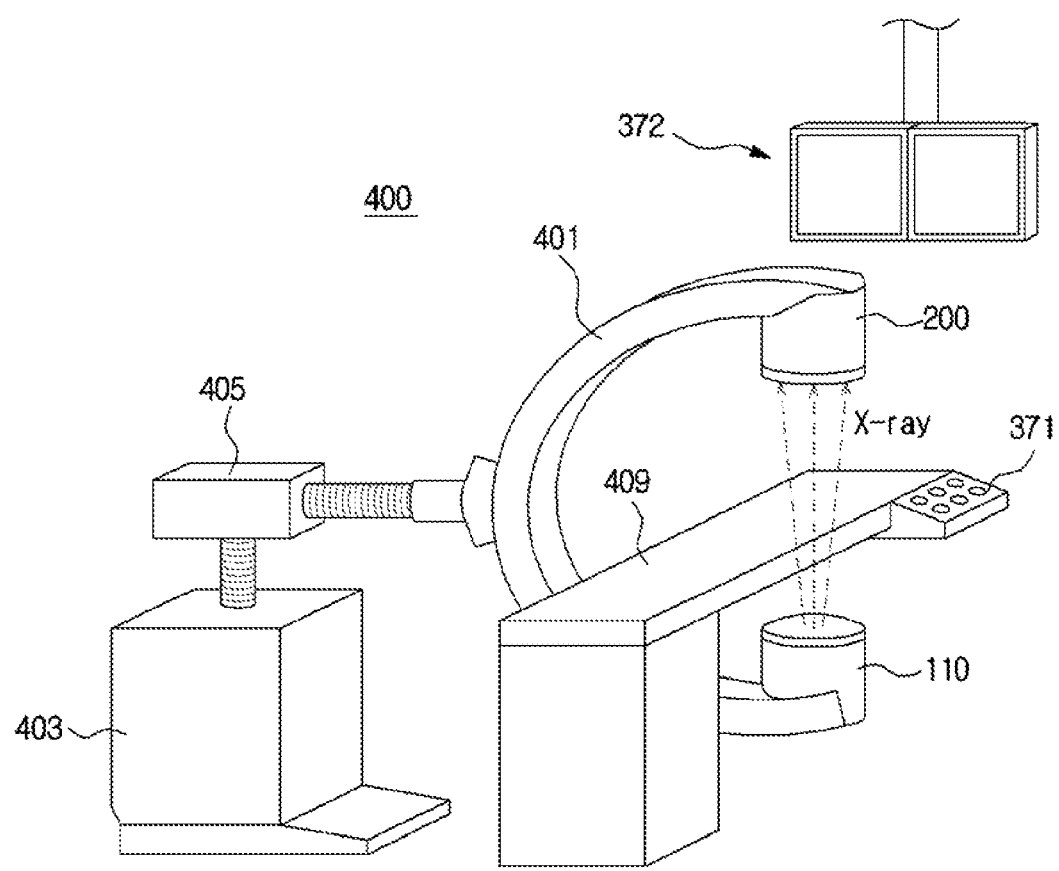
FIG. 12 is an external view of the X-ray imaging apparatus according to an embodiment of the disclosure.

FIG. 3 is a control block diagram of an X-ray generator 100 and an X-ray imaging apparatus 400 (as shown in FIG. 12) including the same, according to an embodiment of the disclosure.

Referring to FIG. 3, the X-ray imaging apparatus 400 may include the X-ray generator 100 to generate X-rays, an X-ray detector 200 to detect the X-rays, and a host device 300 to generate an X-ray image using the detected X-rays and to provide overall control to the X-ray imaging apparatus 400. For example, the host device may include a user interface to receive an input from a user to control various functions of the X-ray imaging apparatus 400 and elements thereof. The host device 300 may also be referred to as a workstation or console.

For example, the host device 300 may include a display and a user interface. The display may include a liquid crystal display (LCD), a light emitting diode (LED) display, an organic light emitting diode (OLED) display, active matrix organic light emitting diode (AMOLED), flexible display, 3D display, a plasma display panel (PDP), a cathode ray tube (CRT) display, and the like, for example. However, the disclosure is not so limited thereto and may include other types of displays. The user interface may include, for example, one or more of a keyboard, a mouse, a joystick, a button, a switch, an electronic pen or stylus, a gesture recognition sensor (e.g., to recognize gestures of a user including movements of a body part), an input sound device or voice recognition sensor (e.g., a microphone to receive a voice command), an output sound device (e.g., a speaker), a track ball, a remote controller, a portable phone (e.g., a cellular or smart phone), a tablet PC, a pedal or footswitch, a virtual-reality device, and the like. The user interface may further include a haptic device to provide haptic feedback to a user. The user interface may also include a touch screen, for example. The display and user interface may be embodied as a single device (e.g., a smart phone, a tablet, or a touch screen display, etc.).

The X-ray generator 100 may include an X-ray tube 110 to generate X-rays, and a high-voltage generator 120 to supply a tube voltage to the X-ray tube 110. A description will now be given of the configuration or arrangement and operation of the X-ray tube 110 with reference to FIG. 4.

Figure 4:
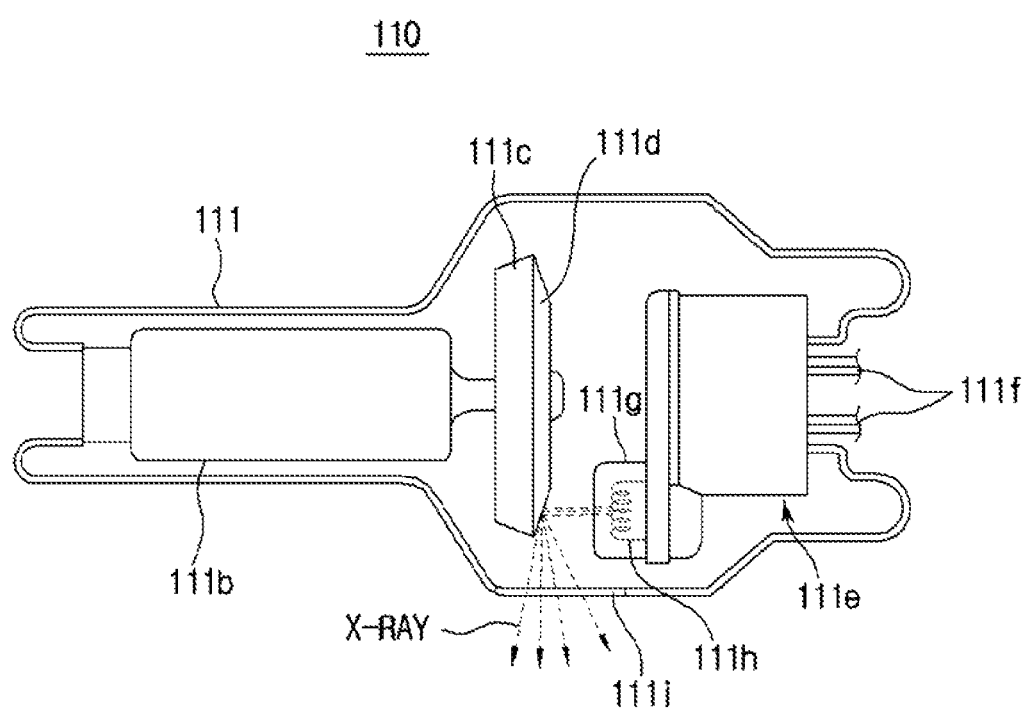
FIG. 4 is a side cross-sectional view of an X-ray tube.

FIG. 4 is a side cross-sectional view of the X-ray tube 110.

Referring to FIG. 4, the X-ray tube 110 may be formed as a bipolar vacuum tube 111 including an anode 111c and a cathode 111e. The cathode 111e may include a filament 111h and a focusing electrode 111g to focus electrons. The focusing electrode 111g may also be referred to as a focusing cup.

The vacuum tube 111 may be evacuated to a high vacuum state of about 10 mmHg and the filament 111h of the cathode 111e may be heated to a high temperature to generate thermoelectrons. The filament 111h may be, for example, a tungsten filament and may be heated by applying a current to an electrically conductive wire 111f connected to the filament 111h.

The anode 111c may be formed of, for example, copper (Cu), and a target material 111d may be embodied as a high-resistance material. For example, the target material 111d may be chromium (Cr), iron (Fe), cobalt (Co), nickel (Ni), tungsten (W), or molybdenum (Mo) and may be coated or located on a surface of the anode 111c facing the cathode 111e. The size of a focal spot may be small if the melting point of the target material 111d is high. Here, the focal spot may refer to an effective focal spot. In addition, the target material 111d may be tilted (or inclined) by a certain angle, and the size of the focal spot may be small if the tilted (or inclined) angle is small.

If a high voltage is applied between the cathode 111e and the anode 111c, thermoelectrons are accelerated and collide with the target material 111d of the anode 111c, thereby generating X-rays. The generated X-rays are radiated outside through a window 111i that may be formed as a thin beryllium (Be) film. In this case, a filter may be located on a front or rear surface of the window 111i to filter X-rays having a certain energy band. For example, if a filter to filter energy having a low-energy band is located, an average of the energy of the radiated X-rays may be increased.

The target material 111d may be rotated by a rotor 111b. If the target material 111d is rotated, compared to a case in which it is fixed, a heat accumulation rate per unit area may be increased by about 10 times or more, and the size of the focal spot may be reduced.

A voltage applied between the cathode 111e and the anode 111c may be referred to as a tube voltage, and the magnitude thereof may be represented as peak kilovolts (kVp). If the tube voltage is increased, the speed of thermoelectrons is increased and thus the energy of X-rays (the energy of photons) generated due to collision of the thermoelectrons with the target material 111d is increased.

A current flowing between the cathode 111e and the anode 111c is referred to as a tube current and may be represented as average current (mA). If the tube current is increased, the number of thermoelectrons colliding with the target material 111d is increased and thus the dose of X-rays (the number of X-ray photons) is increased.

Accordingly, the energy of X-rays may be controlled by the tube voltage and the dose of X-rays may be controlled by the tube current and an X-ray exposure time.

Although not shown in FIG. 4, the vacuum tube 111 may be inserted into a housing filled with insulating oil, and an anode cable and cathode cable are respectively connected to an anode terminal and cathode terminal of the housing to supply a voltage.

Figure 5:
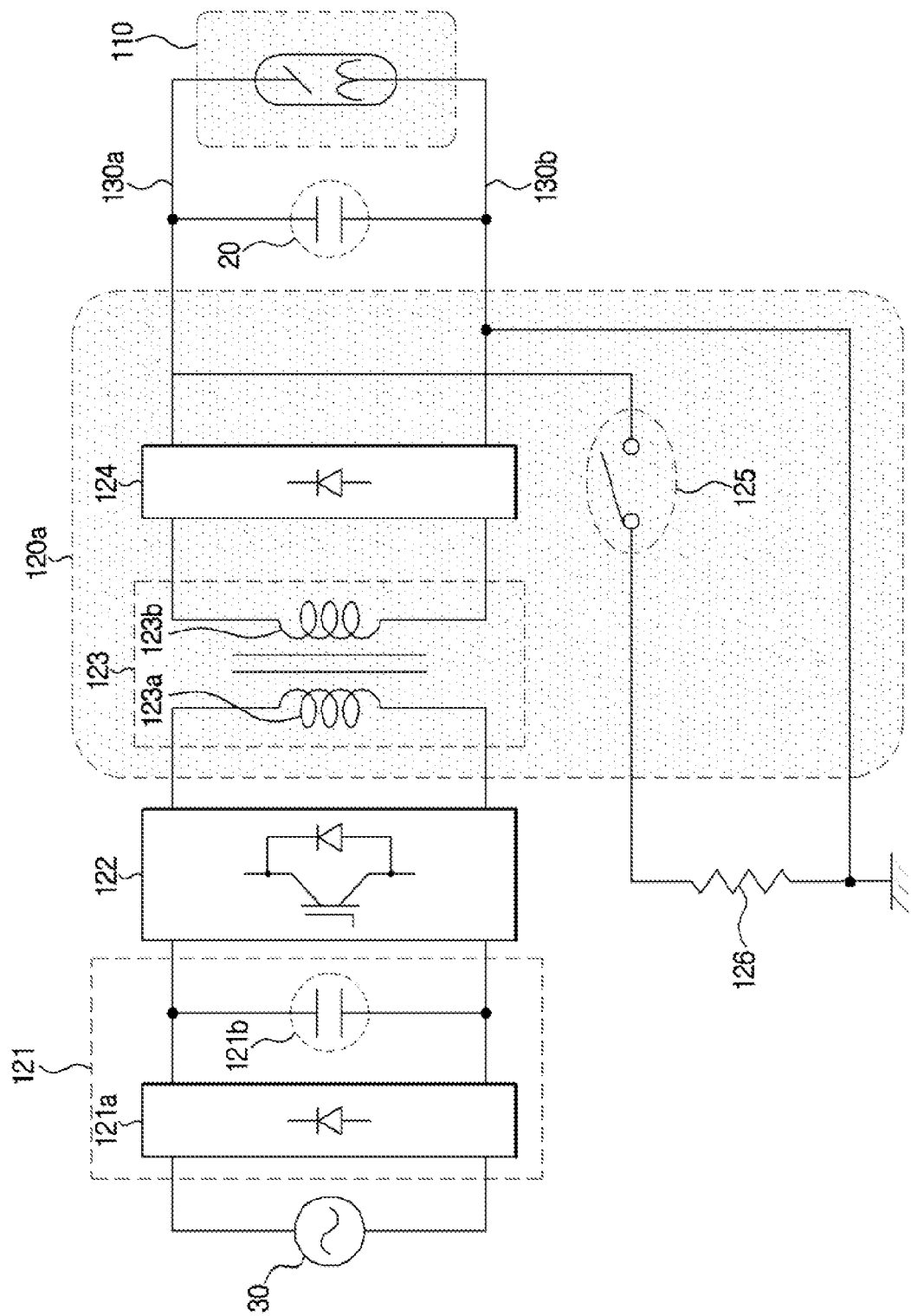
FIG. 5 is a circuit diagram of an example of a high-voltage generator.

FIG. 5 is a circuit diagram of an example of the high-voltage generator 120.

Referring to FIG. 5, the high-voltage generator 120 may include a converter 121 including a rectifier 121a and a smoothing condenser 121b to convert alternating current (AC) power supplied from an external power supply 30 into direct current (DC) power, an inverter 122 to convert the converted DC power into high-frequency AC power of about several ten to about several hundred kHz, a step-up transformer 123 to boost the AC power input to a primary coil 123a to up to about several hundred kV, for example, about 50 to about 150 kV, and to output the boosted AC voltage to a secondary coil 123b, and a rectifier 124 to rectify the boosted AC voltage and to output a tube voltage close to a DC waveform.

As described above, since stray capacitance 20 exists on high-voltage cables 130a and 130b connecting the high-voltage generator 120 and the X-ray tube 110, the high-voltage generator 120 may include a wave tail blocking circuit to block wave tails generated when charges accumulated as the stray capacitance 20 are discharged.

The wave tail blocking circuit may be connected in parallel to an output terminal of the high-voltage generator 120, and may include a switch 125 turned on or off to allow or disallow the flow of charges into the wave tail blocking circuit, and a resistor 126 to consume power generated due to wave tails.

Among circuit elements of the high-voltage generator 120, the step-up transformer 123 and the rectifier 124 to generate a high voltage may be located in a high-voltage tank 120a maintained under vacuum or filled with insulating oil, as illustrated in FIG. 5. This is to insulate the step-up transformer 123 considering that arcs can be generated in a boosting operation.

For example, if the resistor 126 consuming power generated due to wave tails is located in the high-voltage tank 120a, the temperature inside the high-voltage tank 120a may be increased due to heat generated by the resistor 126. As such, the high-voltage tank 120a should be designed to a larger size in consideration of heat capacity.

In addition, if the switch 125 is located in the high-voltage tank 120a as illustrated in FIG. 5, the increased temperature inside the high-voltage tank 120a may influence operational characteristics of the switch 125 formed as a semiconductor switching device, thereby causing a reduction in reliability.

Accordingly, in the high-voltage generator 120 of FIG. 5, by locating the resistor 126 consuming power generated due to wave tails outside the high-voltage tank 120a, the high-voltage tank 120a may have a small size and a reduction in reliability of the switch 125 due to high temperature may be prevented. Here, it will be understood that elements which are disposed inside the high-voltage tank 120a as illustrated in FIG. 5 may be shown by the shaded portion inside of the dashed-lines, while elements which are disposed outside the high-voltage tank 120a as illustrated in FIG. 5 may located outside of the shaded portion inside of the dashed-lines.

In brief, operation of the high-voltage generator 120 of FIG. 5 is as follows. The high-voltage generator 120 generates and applies a tube voltage having a pulse waveform to two terminals of the X-ray tube 110 through the high-voltage cables 130a and 130b, and the switch 125 is turned on at a pulse waveform falling point, i.e., a wave tail generation point, such that charges accumulated as the stray capacitance 20 of the high-voltage cables 130a and 130b discharges may flow into the wave tail blocking circuit.

The charges flowing into the wave tail blocking circuit flow through the resistor 126 located outside the high-voltage tank 120a such that a wave tail voltage is applied to the resistor 126, and the resistor 126 consumes power generated due to wave tails. That is, since charges forming wave tails flow into the wave tail blocking circuit instead of the X-ray tube 110, invalid exposure of an object may be prevented.

In addition, although the resistor 126 is heated due to power consumption, since the resistor 126 is located outside the high-voltage tank 120a, the resistor 126 does not influence operational characteristics of the switch 125 and the high-voltage tank 120a does not need to have a large size.

Besides, when X-rays are generated in a pulse mode to capture X-ray video or images, although the amount of heat generated by the resistor 126 is proportional to the speed of generating X-rays, i.e., a pulse rate, limitation of the pulse rate due to heat may be prevented because the resistor 126 is located outside the high-voltage tank 120a.

Figure 6:
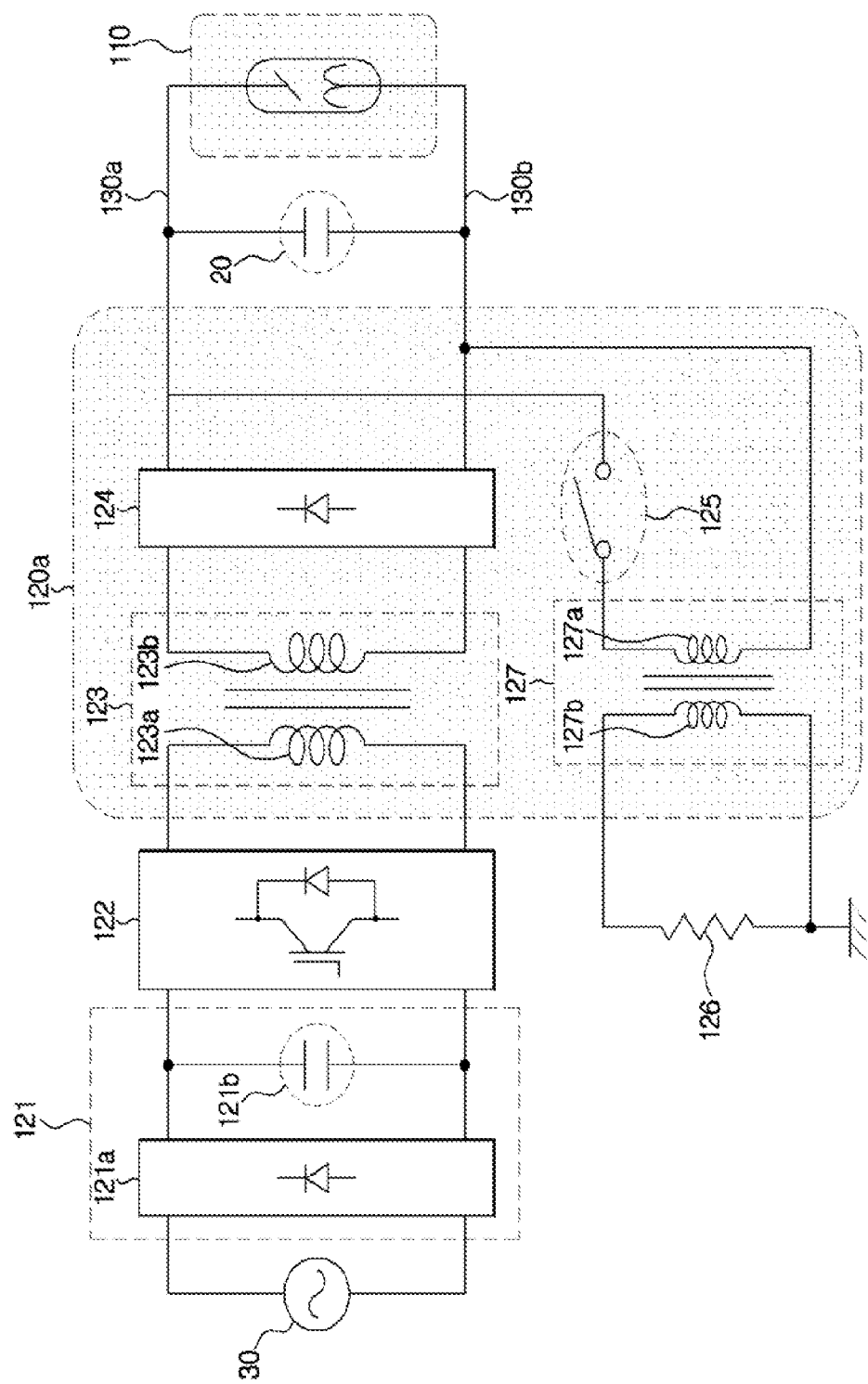
FIG. 6 is a circuit diagram of another example of the high-voltage generator.

FIG. 6 is a circuit diagram of another example of the high-voltage generator 120.

In the high-voltage generator 120, the wave tail blocking circuit may further include a step-down transformer 127 connected between the output terminal of the high-voltage generator 120 and the resistor 126, as illustrated in FIG. 6.

A primary coil 127a of the step-down transformer 127 is connected to the output terminal of the high-voltage generator 120, and a secondary coil 127b of the step-down transformer 127 is connected to the resistor 126.

A voltage input to the wave tail blocking circuit when the switch 125 is turned on is dropped by a turn ratio of the primary coil 127a and the secondary coil 127b through the step-down transformer 127, and power transferred to the resistor 126 through the secondary coil 127b is transformed into heat by the resistor 126. The turn ratio of the primary coil 127a and the secondary coil 127b may be determined in consideration of a voltage drop ratio.

The resistor 126 consuming power generated due to wave tails may be located in the high-voltage tank 120a, however the temperature inside the high-voltage tank 120a may be increased due to heat generated by the resistor 126, and the high-voltage tank 120a may require a larger size in consideration of heat capacity. Further, the increased temperature inside the high-voltage tank 120a may negatively influence operational characteristics of the switch 125. According to the high-voltage generator 120 of FIG. 6, since a dropped voltage is applied to the resistor 126 which is located outside the high-voltage tank 120a, risks caused when a high voltage is applied to the resistor 126 may be reduced.

Figure 7:
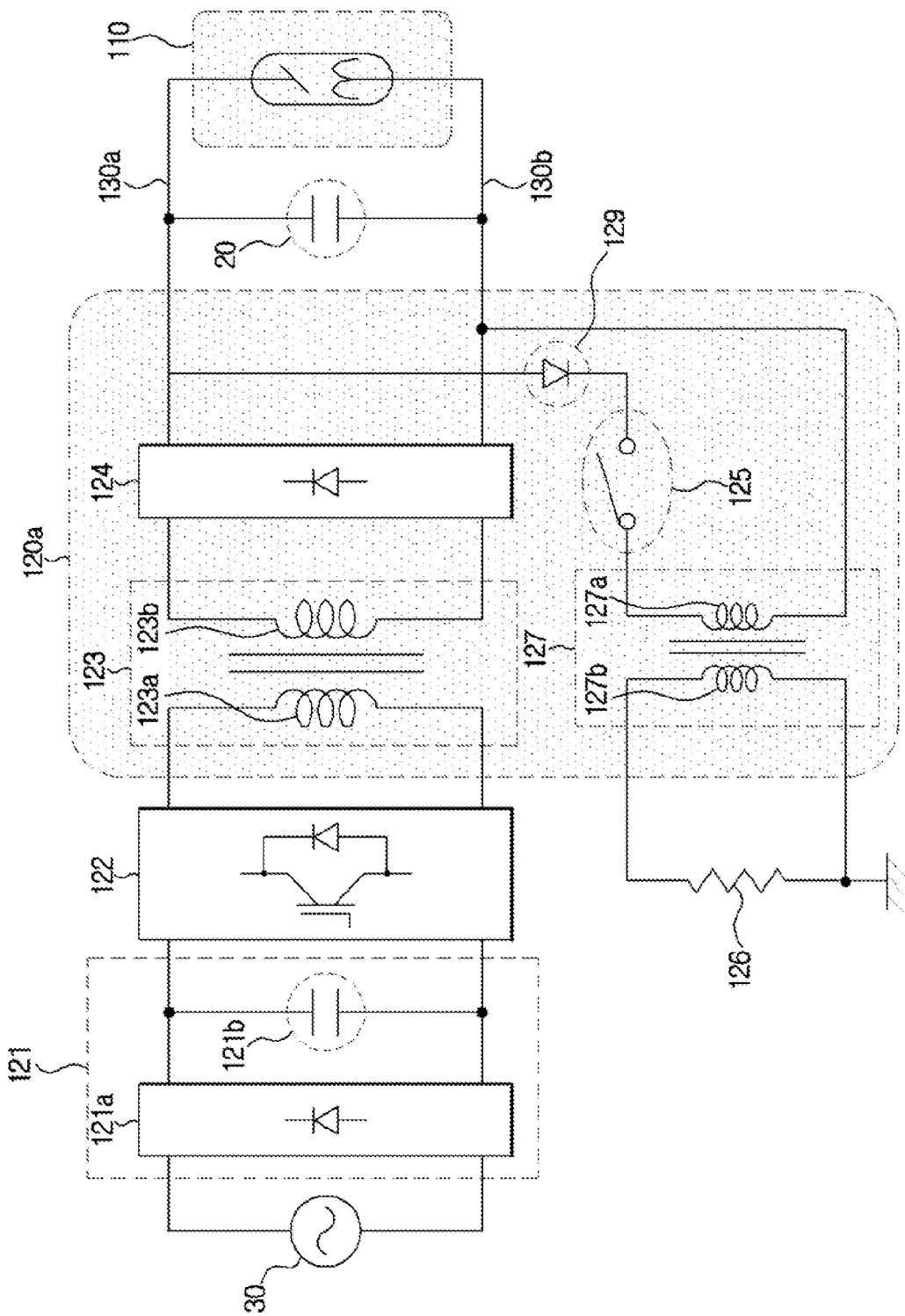
FIG. 7 is a circuit diagram of the high-voltage generator of FIG. 6, to which a diode is added.

FIG. 7 is a circuit diagram of the high-voltage generator 120 of FIG. 6, to which a diode is added.

Referring to FIG. 7, a forward diode 129 may be connected between the output terminal of the high-voltage generator 120 and the switch 125. When the switch 125 is turned on and the step-down transformer 127 drops a voltage, resonance may be generated due to component L (inductance) of coils and component C (capacitance) between the coils and inner wall of the step-down transformer 127. As such, a backward current may be generated from the primary coil 127a toward the X-ray tube 110, but is blocked by the forward diode 129 from being transferred to the X-ray tube 110.

Although the forward diode 129 is connected between the output terminal of the high-voltage generator 120 and the switch 125 in FIG. 7, embodiments of the disclosure are not limited thereto as long as the forward diode 129 is connected between the output terminal of the high-voltage generator 120 and the step-down transformer 127. Accordingly, the forward diode 129 may alternatively or additionally be connected between the switch 125 and the step-down transformer 127.

Figure 8:
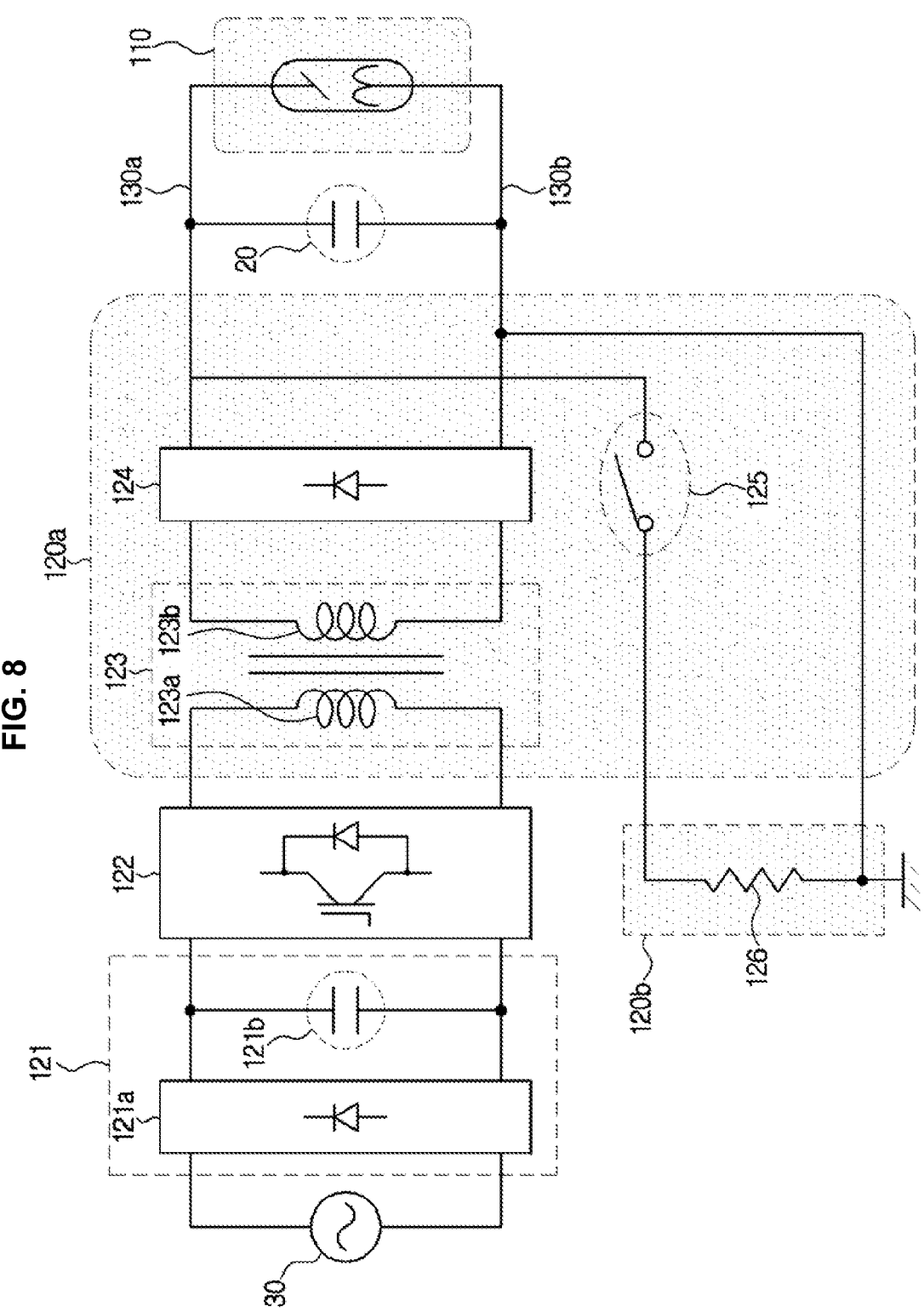
FIG. 8 is a circuit diagram of another example of the high-voltage generator.

FIG. 8 is a circuit diagram of another example of the high-voltage generator 120.

In the high-voltage generator 120, the resistor 126 of the wave tail blocking circuit may be located outside the high-voltage tank 120a and located in an additional sub tank 120b for insulation, as illustrated in FIG. 8.

The sub tank 120b may also be maintained under vacuum or filled with insulating oil, and may be separated from the high-voltage tank 120a accommodating the switch 125.

According to the high-voltage generator 120 of FIG. 8, since the switch 125 is separated from the resistor 126, which is a heater, operational characteristics thereof are not influenced. In addition, since the resistor 126 is located in the additional sub tank 120b, even when the step-down transformer 127 is not formed, risks caused when a high voltage is applied may be prevented. Alternatively, the step-down transformer 127 may still be provided inside the high-voltage tank 120a or inside the sub-tank 120b.

Figure 9A:
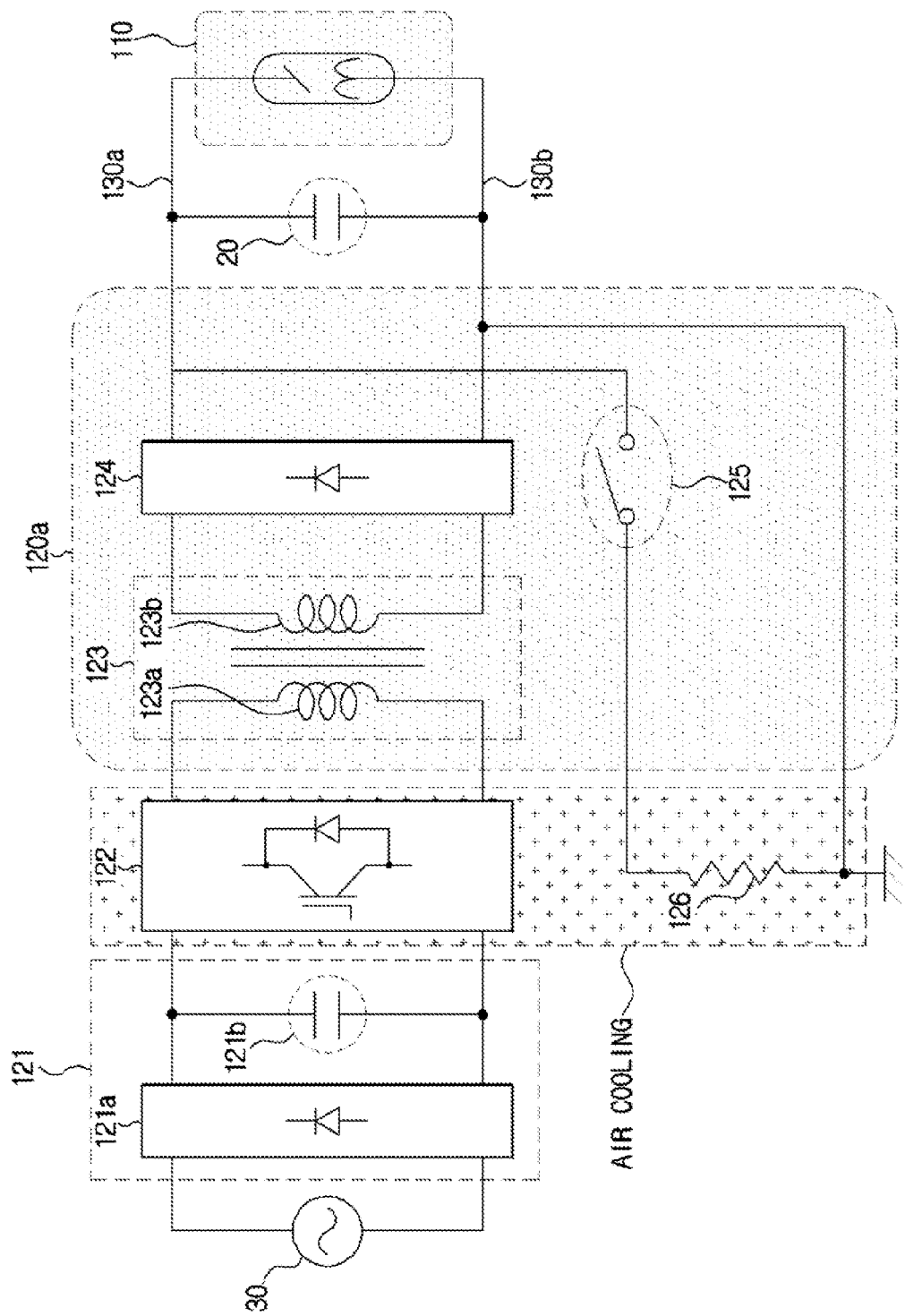
FIGS. 9A and 9B are circuit diagrams of the high-voltage generator capable of air-cooling an external resistor using a cooler of an inverter.
Figure 9B:
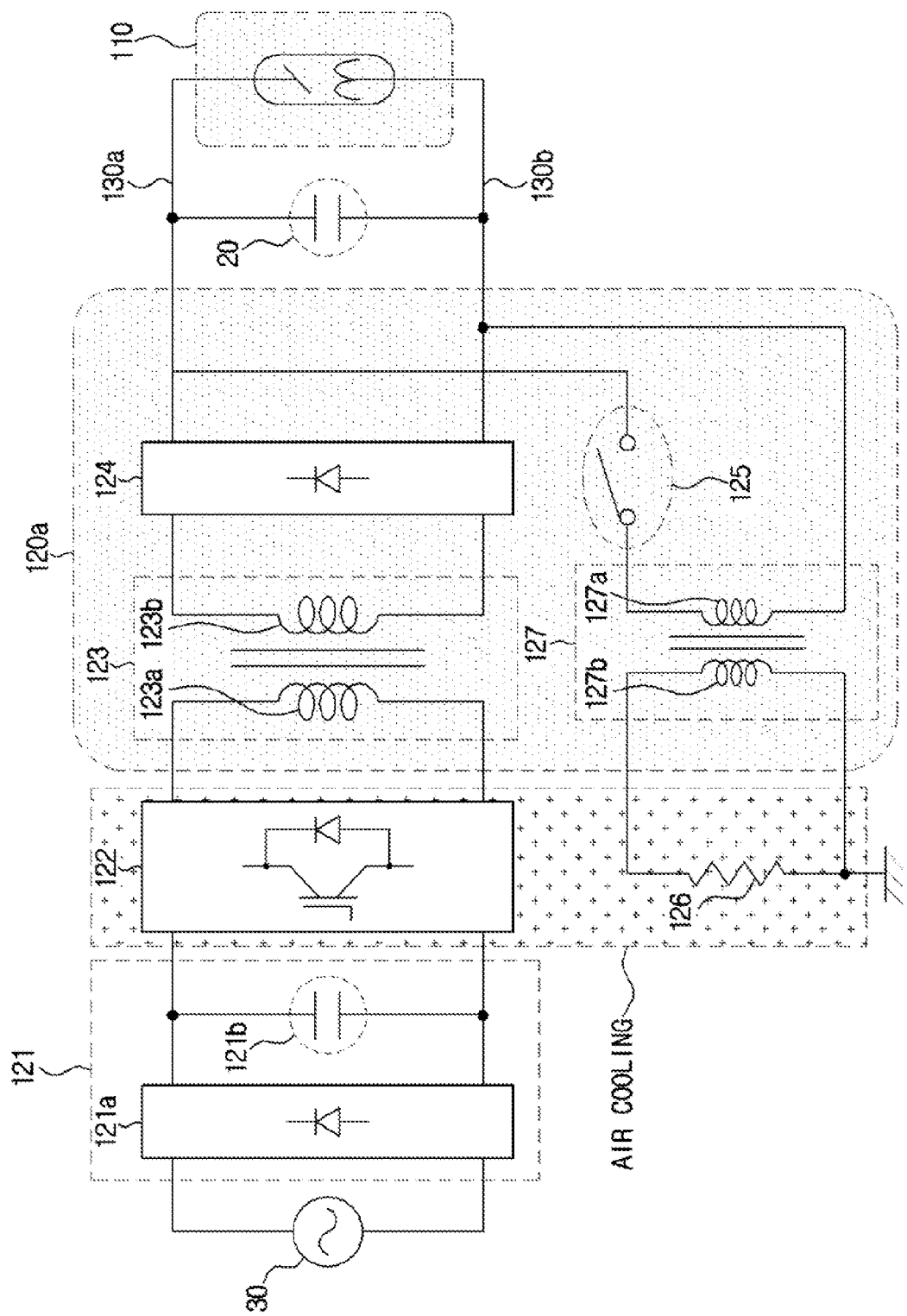

FIGS. 9A and 9B are circuit diagrams of the high-voltage generator 120 capable of air-cooling an external resistor using a cooler of the inverter 122.

As described above, the inverter 122 converts DC power converted by the converter 121, into high-frequency AC power. Accordingly, the inverter 122 generates heat due to a high frequency. Although not shown in FIGS. 9A and 9B a cooler, for example, a cooling fan, to cool the inverter 122 may be included in the high-voltage generator 120.

As illustrated in FIGS. 9A and 9B, if the resistor 126 located outside the high-voltage tank 120a is located in a region to be cooled by the cooler of the inverter 122, i.e., a cooling region of the cooler, the resistor 126 may be cooled together with the inverter 122 in an air cooling manner. That is, a same cooler used to cool the inverter 122 may also be used to cool the resistor 126. In an alternative embodiment, if the resistor 126 is disposed in a sub tank, (e.g., the additional sub tank 120b), it may be possible for cooling air flow from the cooler to be provided to the resistor 126 via a passage or ventilation ducts, etc. Alternatively, sub-tank and/or the resistor 126 may be provided with a separate cooler (e.g., a cooling fan).

Figure 10A:
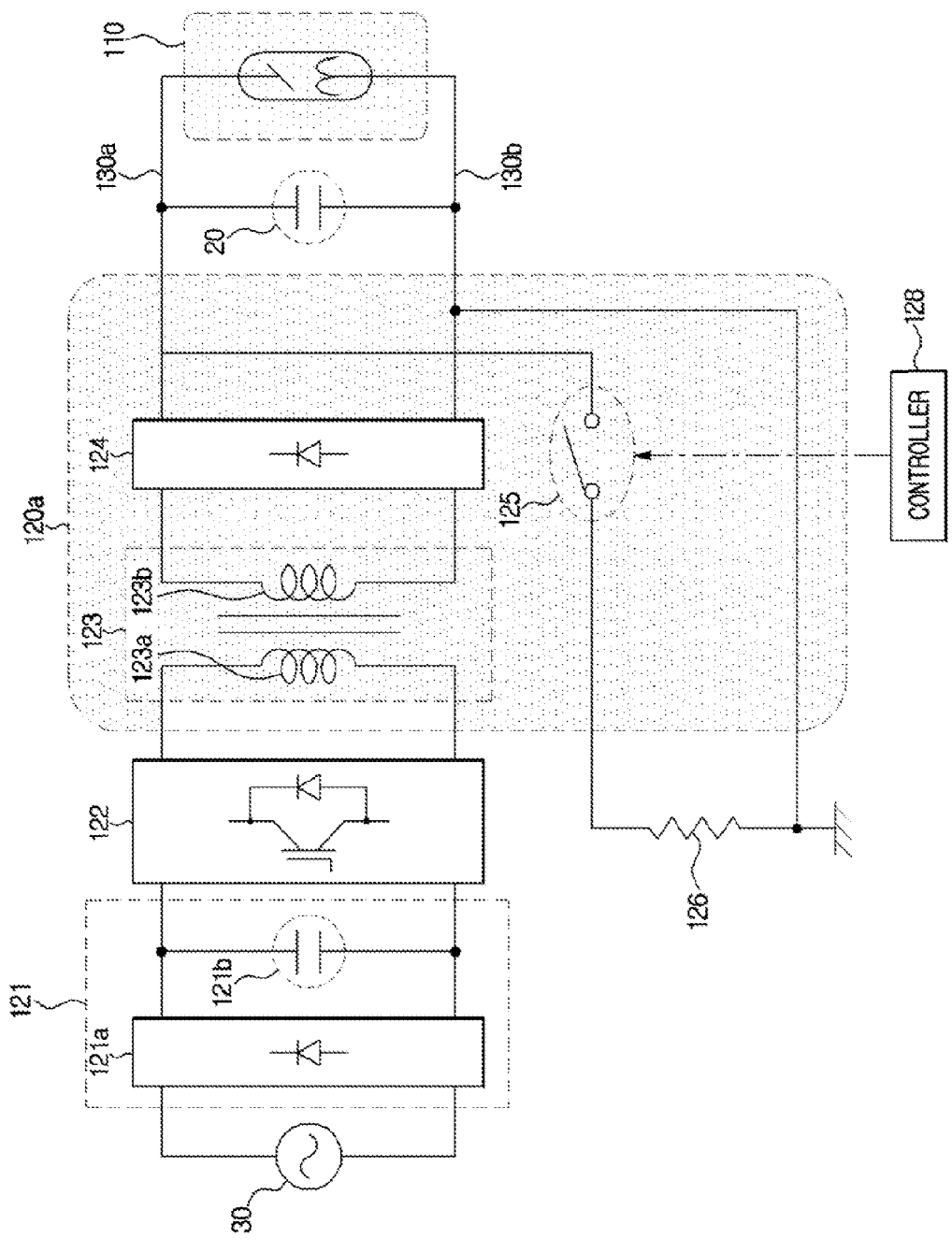
FIGS. 10A to 10C are circuit diagrams of the high-voltage generator further including a controller.
Figure 10B:
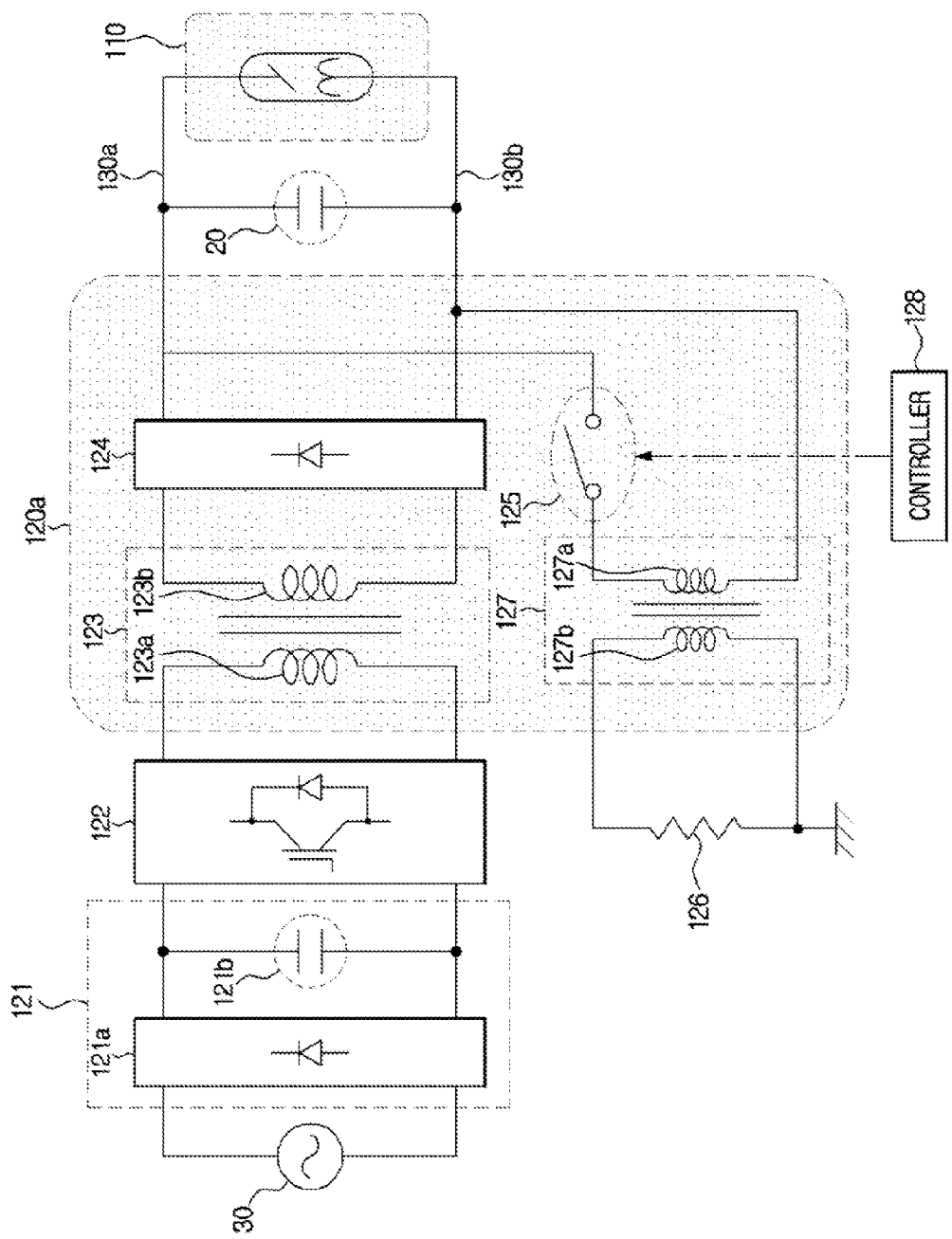
Figure 10C:
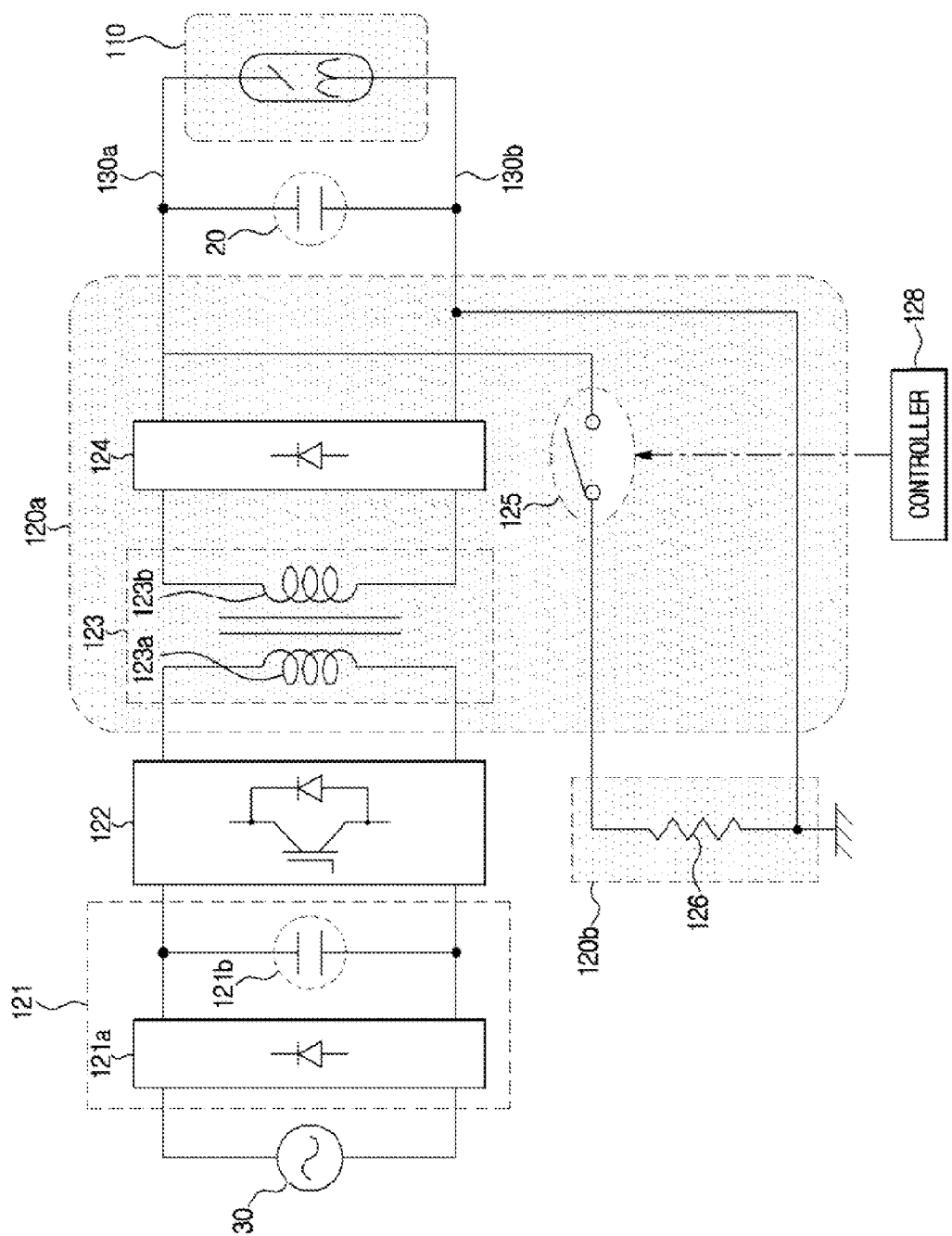
Figure 11:
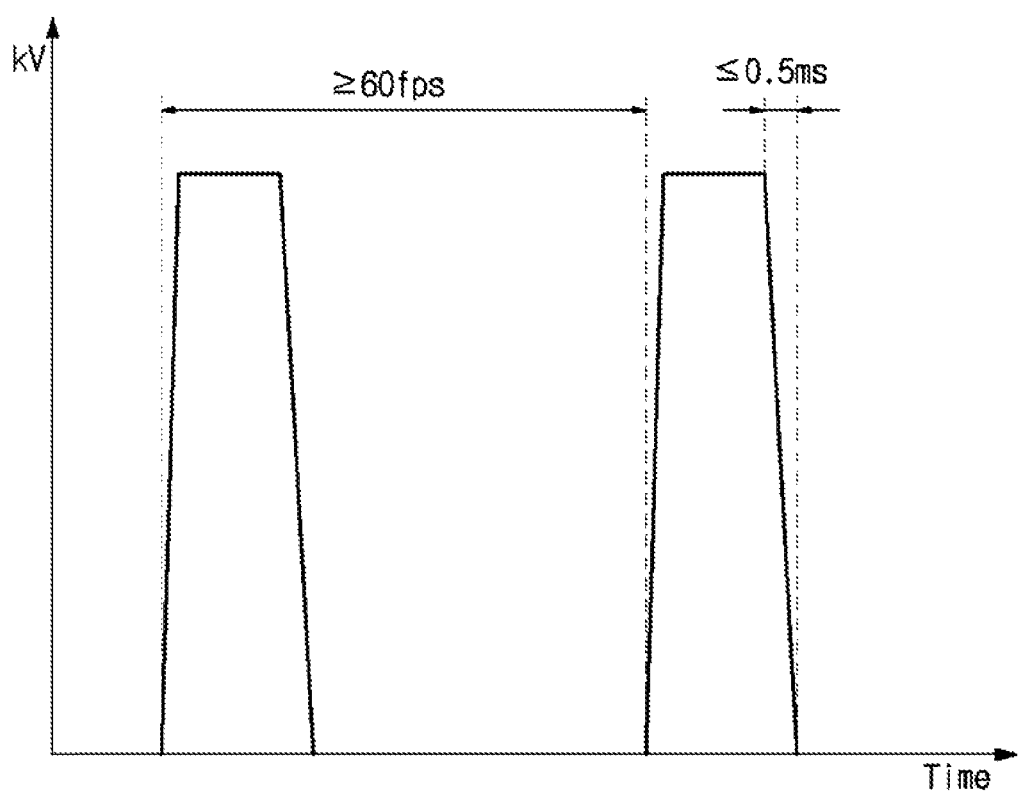
FIG. 11 is a graph showing an effect of eliminating wave tails by applying the X-ray generator according to an embodiment of the disclosure.

FIGS. 10A to 10C are circuit diagrams of the high-voltage generator 120 further including a controller 128, and FIG. 11 is a graph showing an effect of eliminating wave tails by applying the X-ray generator 100 according to an embodiment of the disclosure.

Referring to FIGS. 10A to 10C, the high-voltage generator 120 may further include the controller 128 to control on or off timing of the switch 125. The high-voltage generator 120 of FIG. 10A is obtained by further including the controller 128 in the high-voltage generator 120 of FIG. 5, the high-voltage generator 120 of FIG. 10B is obtained by further including the controller 128 in the high-voltage generator 120 of FIG. 6, and the high-voltage generator 120 of FIG. 10C is obtained by further including the controller 128 in the high-voltage generator 120 of FIG. 8.

Although not shown in FIG. 10B, as described above in relation to FIG. 7, the forward diode 129 may be further included in the circuit diagram of FIG. 10B. For example, the forward diode 129 may be disposed between the output terminal of the high-voltage generator 120 of FIG. 10B and the switch 125 and/or the forward diode 129 may alternatively or additionally be connected between the switch 125 and the step-down transformer 127.

In the high-voltage generators 120 of FIGS. 10A to 10C, elements other than the controller 128 are described above in relation to FIGS. 5 through 8 and thus detailed descriptions thereof are not provided herein.

The controller 128 may be formed as a controller and synchronize a wave tail generation point with an on point of the switch 125. An on point of the switch 125 may correspond to a point in time at which the switch 125 is turned on. An off point of the switch 125 may correspond to a point in time at which the switch 125 is turned off. The wave tail generation point may be a pulse waveform falling point, i.e., a point when output of a high voltage is stopped and charges accumulated as stray capacitance are discharged.

Accordingly, the controller 128 may determine the pulse waveform falling point using information about a pulse rising point and a pulse width. For example, the controller 128 may set the pulse waveform falling point as the on point of the switch 125, and send an on signal to the switch 125 at the pulse waveform falling point.

The controller 128 may send an off signal to the switch 125 at a point when the charges are completely discharged or a new pulse is generated. The latter case will now be described in detail.

When the X-ray generator 100 generates X-rays in a pulse mode to capture X-ray video or images, the controller 128 may determine a pulse waveform rising point using information about a preset pulse rate, and set the pulse waveform rising point as an off point of the switch 125 to send an off signal to the switch 125 at the pulse waveform rising point.

In addition to on or off control of the switch 125, the controller 128 may control the magnitude of a tube voltage generated by the high-voltage generator 120. To this end, the controller 128 may use a user control command, which may be input via a user interface included in the host device 300 or separately formed to control the X-ray generator 100. Alternatively, the controller 128 may automatically control the magnitude of the tube voltage using an auto exposure control function.

The high-voltage generator 120 may further include a circuit to generate and supply a filament current to the filament 111h of the X-ray tube 110. As such, the controller 128 may control the amplitude of the tube current and an exposure time as well as the magnitude of the tube voltage.

If the X-ray generator 100 according to any of the disclosed embodiments is applied, the switch 125 may be turned on at a wave tail generation point and charges accumulated as the stray capacitance 20 may be rapidly discharged through the resistor 126. As such, a wave tail remaining time may be reduced to about 0.5 ms or less as illustrated in FIG. 11, and thus a frame rate equal to or greater than 60 fps may be achieved.

For example, if the resistor 126 is located outside the high-voltage tank 120a as illustrated in FIGS. 5 to 8, even when a tube voltage is generated according to a high frame rate, heat inside the high-voltage tank 120a does not cause any problems.

FIG. 12 is an external view of the X-ray imaging apparatus 400 according to an embodiment of the disclosure.

The X-ray imaging apparatus 400 including the above-described X-ray generator 100 may be applied to the field of general X-ray imaging (radiography) and the field of X-ray video.

X-ray video may be captured using a continuous exposure mode to continuously generate X-rays, or a pulse mode to generate X-rays according to repeated short pulses. The pulse mode may reduce the dose of X-rays and motion blur but is greatly influenced by wave tails due to repetition of short pulses.

However, when the X-ray imaging apparatus 400 captures X-ray video in a pulse mode, since the wave tail blocking circuit rapidly consumes power generated due to wave tails, a high frame rate may be achieved and invalid exposure of an object may be effectively reduced.

For example, the X-ray imaging apparatus 400 may have a C-arm structure as illustrated in FIG. 12. The X-ray tube 110 and the X-ray detector 200 may be mounted on two ends of a C-arm 401. The C-arm 401 may be connected to a body 403 through a connection shaft 405 and may be rotated in an orbital direction.

A patient table 409 may be located between the X-ray tube 110 and the X-ray detector 200. When an object is located on the patient table 409, the X-ray tube 110 radiates X-rays to the object and the X-ray detector 200 obtains an X-ray image of the object by detecting the radiated X-rays.

The X-ray imaging apparatus 400 may obtain real-time video of the object. As such, a user may perform diagnosis or a medical procedure while viewing a display unit 372 which may include one or more screens to display a variety of images required for diagnosis or a medical procedure. A command to control the X-ray imaging apparatus 400 may be input via an input unit 371.

The X-ray imaging apparatus 400 shown in FIG. 12 is only provided as an example, and the disclosure is not limited to the configuration of the X-ray imaging apparatus 400 shown in FIG. 12. For example, the X-ray imaging apparatus 400 may be arranged differently such that the X-ray tube 110 and the X-ray detector 200 are positioned in an opposite manner, or in a horizontal arrangement, and X-rays are emitted in other directions (e.g., horizontally, vertically, etc.). Further, the connection arm need not be a C-arm structure. Also, the patient table 409, if needed, may not be horizontally arranged, but instead, may be arranged in a vertical or inclined manner, for example. Further, X-rays may be taken of any kind of object, including a person, animal, or of materials (e.g., a shipping container, luggage, etc.).

The display unit 372 may include a liquid crystal display (LCD), a light emitting diode (LED) display, an organic light emitting diode (OLED) display, active matrix organic light emitting diode (AMOLED), flexible display, 3D display, a plasma display panel (PDP), a cathode ray tube (CRT) display, and the like, for example. However, the disclosure is not so limited thereto and may include other types of displays.

The input unit 371 may include, for example, one or more of a keyboard, a mouse, a joystick, a button, a switch, an electronic pen or stylus, a gesture recognition sensor (e.g., to recognize gestures of a user including movements of a body part), an input sound device or voice recognition sensor (e.g., a microphone to receive a voice command), an output sound device (e.g., a speaker), a track ball, a remote controller, a portable phone (e.g., a cellular or smart phone), a tablet PC, a pedal or footswitch, a virtual-reality device, and the like. The input unit 371 may further include a haptic device to provide haptic feedback to a user. The input unit 371 may also include a touch screen, for example. The display unit 372 and input unit 371 may be embodied as a single device (e.g., a smart phone, a tablet, or a touch screen display, etc.).

A description will now be given of a method of controlling the X-ray generator 100, according to an embodiment of the disclosure.

Figure 13:
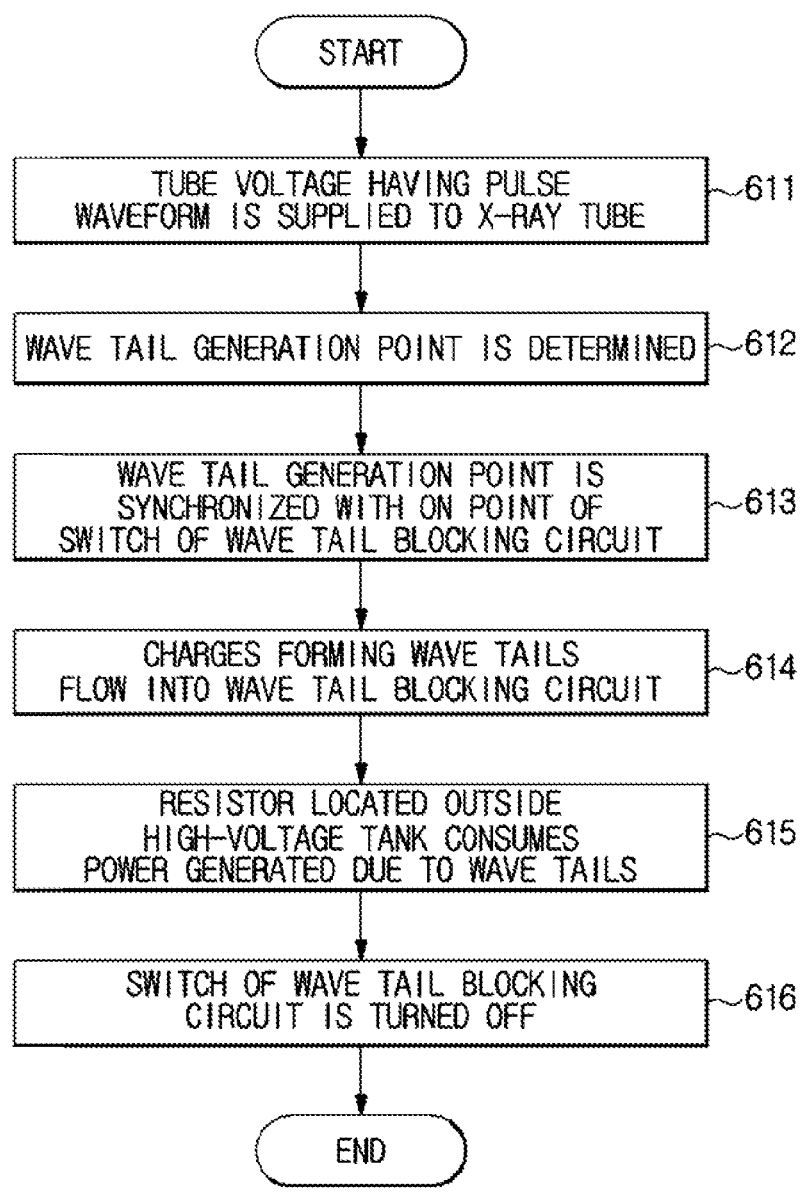
FIG. 13 is a flowchart of a method of controlling the X-ray generator, according to an embodiment of the disclosure.

FIG. 13 is a flowchart of a method of controlling the X-ray generator 100, according to an embodiment of the disclosure. For example, the method shown in FIG. 13 may be implemented using any one of the high-voltage generator 120 of FIG. 5 to FIG. 8.

Referring to FIG. 13, a tube voltage having a pulse waveform may be supplied to the X-ray tube 110 (611). To this end, if AC power is supplied from the external power supply 30 and input to the high-voltage generator 120, the converter 121 converts the AC power into DC power, the inverter 122 converts the converted DC power into high-frequency AC power of about several ten to about several hundred kHz, the step-up transformer 123 boosts the AC voltage according to a turn ratio, and the rectifier 124 rectifies the boosted AC voltage close to a DC waveform and supplies the rectified voltage to the X-ray tube 110.

The controller 128 may determine a wave tail generation point (612). Since the stray capacitance 20 exists on the high-voltage cables 130a and 130b connecting the high-voltage generator 120 and the X-ray tube 110, if the tube voltage having a pulse waveform is completely output, charges accumulated as the stray capacitance 20 are discharged and thus wave tails are generated. Accordingly, the controller 128 may determine the wave tail generation point using a pulse rising point and a pulse width.

The wave tail generation point may be synchronized with an on point of the switch 125 of the wave tail blocking circuit (613). For example, a pulse waveform falling point may be set as the on point of the switch 125, and an on signal may be sent to the switch 125 at the pulse waveform falling point.

If or when the switch 125 is turned on, charges forming wave tails flow into the wave tail blocking circuit (614).

The charges pass through the resistor 126 which may be located outside the high-voltage tank 120a, and the resistor 126 consumes power generated due to wave tails and generates heat (615). For example, the resistor 126 located outside the high-voltage tank 120a may be located in the additional sub tank 120b to prevent risks caused when a high voltage is applied.

If or when the charges are completely discharged, the controller 128 turns off the switch 125 of the wave tail blocking circuit (616). Specifically, the controller 128 may send an off signal to the switch 125 at a point when the charges are completely discharged or a new pulse is generated. For example, when the X-ray generator 100 generates X-rays in a pulse mode to capture X-ray video or images, the controller 128 may determine a pulse waveform rising point using information about a preset pulse rate, and send an off signal to the switch 125 at the pulse waveform rising point.

When the X-ray generator 100 generates X-rays in a pulse mode, operations 611 to 616 may be repeated until the X-rays are completely generated.

Figure 14:
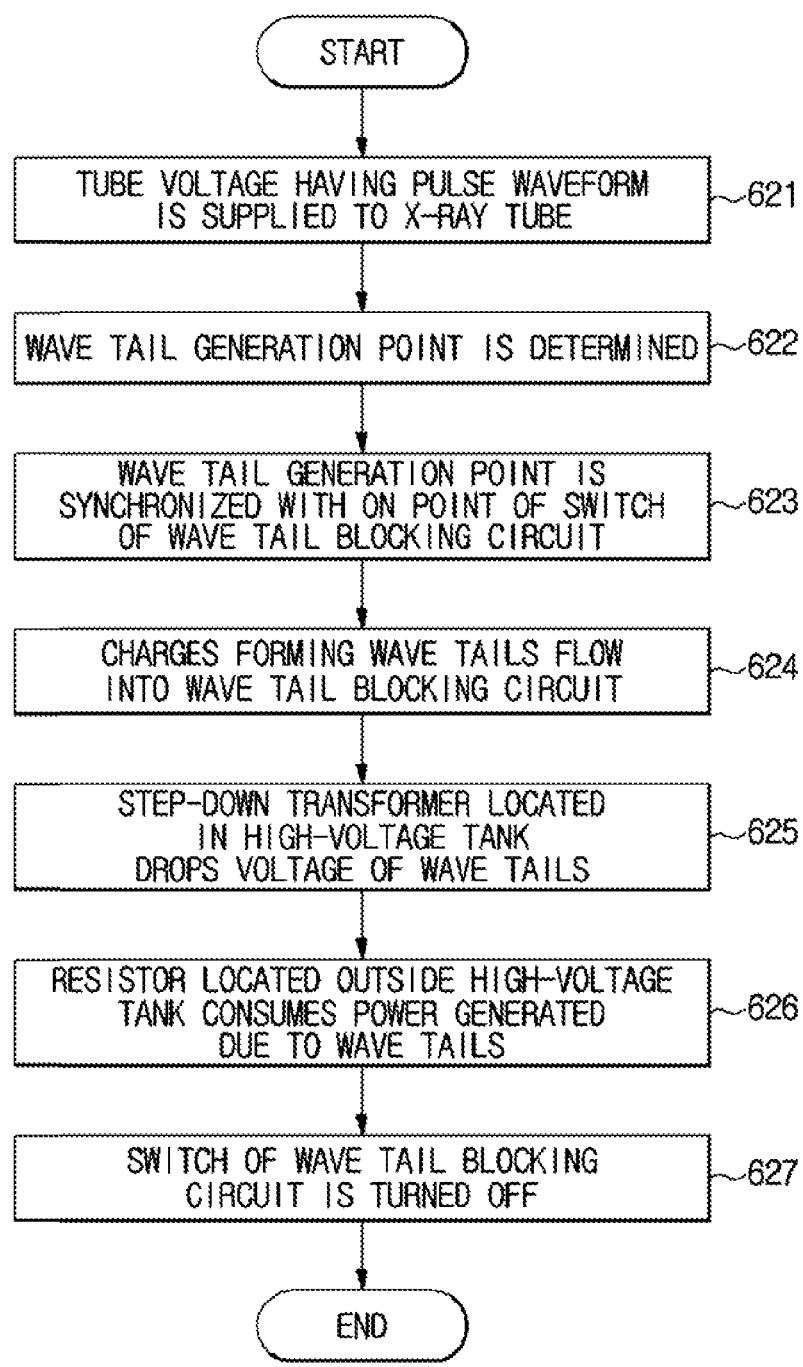
FIG. 14 is a flowchart of a method of controlling the X-ray generator further including a step-down transformer, according to an embodiment of the disclosure.

FIG. 14 is a flowchart of a method of controlling the X-ray generator 100 further including the step-down transformer 127, according to an embodiment of the disclosure. For example, the method shown in FIG. 14 may be implemented using any one of the high-voltage generator 120 of FIG. 6 to FIG. 7.

Referring to FIG. 14, a tube voltage having a pulse waveform is supplied to the X-ray tube 110 (621). To this end, if AC power is supplied from the external power supply 30 and input to the high-voltage generator 120, the converter 121 converts the AC power into DC power, the inverter 122 converts the converted DC power into high-frequency AC power of about several ten to about several hundred kHz, the step-up transformer 123 boosts the AC voltage according to a turn ratio, and the rectifier 124 rectifies the boosted AC voltage close to a DC waveform and supplies the rectified voltage to the X-ray tube 110.

The controller 128 may determine a wave tail generation point (622). Since the stray capacitance 20 exists on the high-voltage cables 130a and 130b connecting the high-voltage generator 120 and the X-ray tube 110, if the tube voltage having a pulse waveform is completely output, charges accumulated as the stray capacitance 20 are discharged and thus wave tails are generated. Accordingly, the controller 128 may determine the wave tail generation point using a pulse rising point and a pulse width.

The wave tail generation point may be synchronized with an on point of the switch 125 of the wave tail blocking circuit (623). For example, a pulse waveform falling point may be set as the on point of the switch 125, and an on signal may be sent to the switch 125 at the pulse waveform falling point.

If or when the switch 125 is turned on, charges forming wave tails flow into the wave tail blocking circuit (624).

The step-down transformer 127 located in the high-voltage tank 120a drops the voltage of the wave tails (625). The voltage of the wave tails is dropped by a turn ratio of the primary coil 127a and the secondary coil 127b through the step-down transformer 127.

The dropped voltage is applied to the resistor 126 which may be located outside the high-voltage tank 120a, and the resistor 126 consumes power generated due to wave tails and generates heat (626). Since the dropped voltage is applied to the resistor 126 located outside the high-voltage tank 120a, risks caused when a high voltage is applied to the resistor 126 may be reduced.

If or when the charges are completely discharged, the controller 128 turns off the switch 125 of the wave tail blocking circuit (627). Specifically, the controller 128 may send an off signal to the switch 125 at a point when the charges are completely discharged or a new pulse is generated. The switch 125 may be turned off as described above. When the X-ray generator 100 generates X-rays in a pulse mode, operations 621 to 627 may be repeated until the X-rays are completely generated.

Additionally, though not shown in FIG. 14, when the switch 125 is turned on, a forward diode 129 as described with respect to FIG. 7, may block backward current generated from the primary coil 127a from being transferred toward the X-ray tube 110.

According to the above-described example embodiments, the X-ray generator, the X-ray imaging apparatus including the X-ray generator, and the method of controlling the X-ray generator, may effectively reduce invalid exposure of an object by rapidly blocking wave tails from being supplied to an X-ray tube.

In addition, a reduction in the reliability of a semiconductor switching device due to heating of a resistor may be prevented by separating the semiconductor switching device from the resistor.

Additionally, a high-voltage tank may have a small size by locating a resistor, which acts as a heater, outside the high-voltage tank, and heat accumulation of an X-ray tube may be reduced and thus throughput of radiography may be increased by rapidly discharging charges forming wave tails.

As is apparent from the above description, in an X-ray generator, an X-ray imaging apparatus including the X-ray generator, and in a method of controlling the X-ray generator, according to the example embodiments of the disclosure, wave tails, which do not contribute to the quality of an X-ray image, may be blocked from being supplied to an X-ray tube and thus invalid and/or additional exposure caused due to the wave tails may be reduced.

The apparatuses and methods according to the above-described example embodiments may use one or more processors. For example, the controller may be embodied as a processing device which may be implemented using one or more general-purpose or special purpose computers, and may include, for example, one or more of a processor, a controller and an arithmetic logic unit, a central processing unit (CPU), a graphics processing unit (GPU), a digital signal processor (DSP), a microcomputer, a field programmable array, a programmable logic unit, an application-specific integrated circuit (ASIC), a microprocessor or any other processing device capable of transmitting, receiving, and/or executing instructions in a defined manner.

Aspects of the above-described embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, USB memory, and the like. Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Aspects of the above-described embodiments may be implemented over a wired or wireless network, or a combination thereof. The network may include a local area network (LAN), wireless local area network (WLAN), wide area network (WAN), personal area network (PAN), virtual private network (VPN), or the like. For example, wireless communication between elements of the example embodiments may be performed via a wireless LAN, Wi-Fi, Bluetooth, Zigbee, Wi-Fi direct (WFD), ultra wideband (UWB), infrared data association (IrDA), Bluetooth low energy (BLE), near field communication (NFC), a radio frequency (RF) signal, and the like. For example, wired communication between elements of the example embodiments may be performed via a pair cable, a coaxial cable, an optical fiber cable, an Ethernet cable, and the like.

Although example embodiments of the disclosure have been shown and described, it would be appreciated by those skilled in the art that changes may be made to these embodiments without departing from the principles and spirit of the disclosure, the scope of which is defined in the claims and their equivalents.

What is claimed is:

1. An X-ray generator comprising:
   an X-ray tube to generate X-rays; and
   a high-voltage generator to supply a voltage to the X-ray tube, the high-voltage generator comprising:
      a high-voltage tank including circuit elements disposed inside the high-voltage tank to generate the voltage supplied to the X-ray tube, the circuit elements disposed inside the high-voltage tank including a switch connected in parallel to first and second output terminals of the high-voltage tank, the switch including a first switch terminal connected to the first output terminal of the high-voltage tank; and
      a resistor, connected in series to the switch, and disposed outside the high-voltage tank to receive a wave tail voltage according to an on or off status of the switch, the resistor including a first resistor terminal connected to the second output terminal of the high-voltage tank.

2. The X-ray generator according to claim 1, wherein the high-voltage tank circuit elements further comprise:

a step-up transformer to boost power supplied from a power supply to a high voltage; and
a rectifier to rectify the boosted power.

3. The X-ray generator according to claim 2, wherein the high-voltage generator further comprises:
a converter to convert alternating current (AC) power supplied from the power supply, into direct current (DC) power; and
an inverter to convert the converted DC power into high-frequency AC power.

4. The X-ray generator according to claim 3, further comprising a cooler to cool the inverter,
wherein the resistor is located in a cooling region of the cooler to be cooled together with the inverter.

5. The X-ray generator according to claim 1, wherein the resistor is located in an insulated sub tank.

6. The X-ray generator according to claim 1, wherein the high-voltage generator supplies the voltage to the X-ray tube according to a preset pulse rate and a pulse width.

7. The X-ray generator according to claim 6, further comprising a controller to control the on or off status of the switch.

8. The X-ray generator according to claim 7, wherein the controller synchronizes a wave tail generation point with an on point of the switch, and the resistor receives the wave tail voltage when the switch is turned on.

9. The X-ray generator according to claim 8, wherein the controller synchronizes a wave tail extinction point or a next pulse rising point with an off point of the switch.

10. The X-ray generator according to claim 9, wherein the controller determines the on point and the off point of the switch based on the preset pulse rate and the pulse width.

11. An X-ray generator comprising:
an X-ray tube to generate X-rays; and
a high-voltage generator to supply a voltage to the X-ray tube, the high-voltage generator comprising:
a high-voltage tank to generate the voltage;
a switch connected to an output terminal of the high-voltage tank;
a resistor located outside the high-voltage tank to receive a wave tail voltage according to an on or off status of the switch; and
a step-down transformer to drop the wave tail voltage.

12. The X-ray generator according to claim 11, wherein the switch and the step-down transformer are located in the high-voltage tank.

13. The X-ray generator according to claim 12, wherein the step-down transformer has a primary coil connected to the output terminal of the high-voltage tank and a secondary coil connected to the resistor.

14. The X-ray generator according to claim 11, wherein the high-voltage generator further comprises a forward diode located between the output terminal of the high-voltage tank and the step-down transformer.

15. The X-ray generator according to claim 1, wherein
the first output terminal of the high-voltage tank corresponds to an anode output terminal connected to an anode of the X-ray tube,
the second output terminal of the high-voltage tank corresponds to a cathode output terminal connected to a cathode of the X-ray tube,
the first switch terminal of the switch is connected to the anode output terminal,
the first resistor terminal of the resistor is connected to the cathode output terminal, and
a second switch terminal of the switch is connected to a second resistor terminal of the resistor.

16. An X-ray imaging apparatus comprising:
an X-ray generator to generate X-rays; and
an X-ray detector to detect the X-rays generated by the X-ray generator, the X-ray generator comprising:
an X-ray tube to generate the X-rays; and
a high-voltage generator to supply a voltage to the X-ray tube, the high-voltage generator comprising:
a high-voltage tank including circuit elements disposed inside the high-voltage tank to generate the voltage supplied to the X-ray tube, the circuit elements disposed inside the high-voltage tank including a switch connected in parallel to first and second output terminals of the high-voltage tank, the switch including a first switch terminal connected to the first output terminal of the high-voltage tank; and
a resistor, connected in series to the switch, and disposed outside the high-voltage tank to receive a wave tail voltage according to an on or off status of the switch, the resistor including a first resistor terminal connected to the second output terminal of the high-voltage tank.

17. The X-ray imaging apparatus according to claim 16, wherein the resistor is located in an insulated sub tank.

18. The X-ray imaging apparatus according to claim 16, wherein the high-voltage generator further comprises:
a converter to convert alternating current (AC) power supplied from a power supply, into direct current (DC) power;
an inverter to convert the converted DC power into high-frequency AC power; and
a cooler to cool the inverter and the resistor.

19. An X-ray imaging apparatus comprising:
an X-ray generator to generate X-rays; and
an X-ray detector to detect the X-rays generated by the X-ray generator, the X-ray generator comprising:
an X-ray tube to generate the X-rays; and
a high-voltage generator to supply a voltage to the X-ray tube, the high-voltage generator comprising:
a high-voltage tank to generate the voltage;
a switch connected to an output terminal of the high-voltage tank;
a resistor located outside the high-voltage tank to receive a wave tail voltage according to an on or off status of the switch; and
a step-down transformer to drop the wave tail voltage.

20. A method of controlling an X-ray generator comprising an X-ray tube to generate X-rays, and a high-voltage generator to supply a voltage having a pulse waveform to the X-ray tube, the method comprising:
determining a wave tail generation point of the pulse waveform occurs when output of a predetermined voltage level has stopped and charges accumulated as stray capacitance are discharged;
synchronizing an on point of a switch disposed inside of a high-voltage tank and connected to an output terminal of the high-voltage tank, with the occurrence of the wave tail generation point; and
closing the switch when the switch is turned on, and applying a wave tail voltage to a resistor disposed outside of the high-voltage tank,
wherein
the switch includes a first switch terminal connected to one of an anode output terminal connected to an anode of the X-ray tube and an cathode output terminal connected to a cathode of the X-ray tube, and the resistor includes a first resistor terminal connected to the other one of the anode output terminal and the cathode output terminal.

21. The method according to claim 20, further comprising synchronizing a wave tail extinction point or a next pulse rising point with an off point of the switch.

22. The method according to claim 21, wherein the resistor is located in an insulated sub tank.

23. The method according to claim 20, further comprising:
converting alternating current (AC) power supplied from a power supply, into direct current (DC) power;
converting, using an inverter disposed in the high-voltage generator, the converted DC power into high-frequency AC power; and
cooling the inverter and the resistor, using a same cooler.

24. A method of controlling an X-ray generator comprising an X-ray tube to generate X-rays, and a high-voltage generator to supply a voltage having a pulse waveform to the X-ray tube, the method comprising:
determining a wave tail generation point of the pulse waveform;
synchronizing an on point of a switch connected to an output terminal of a high-voltage tank, with the wave tail generation point;
when the switch is turned on, applying a wave tail voltage to a resistor located outside the high-voltage tank, and dropping the wave tail voltage using a step-down transformer located in the high-voltage tank; and
applying the dropped wave tail voltage to the resistor.

25. The method according to claim 24, further comprising:
when the switch is turned on, blocking backward current generated from a primary coil of the step-down transformer from being transferred toward the X-ray tube, using a forward diode.

26. An X-ray generator comprising:
an X-ray tube to generate X-rays, the X-ray tube including an anode connected to an anode output terminal and a cathode connected to a cathode output terminal; and
a high-voltage generator to supply a voltage to the X-ray tube; and
a wave tail blocking circuit connected in parallel to an output terminal of the high voltage generator to prevent wave tails from being supplied to the X-ray tube, the wave tail blocking circuit comprising:
a switch, disposed inside of a high voltage tank of the high-voltage generator, which is used to control a flow of charges accumulated as stray capacitance into the wave tail blocking circuit based on an output of the voltage supplied to the X-ray tube, the switch including a first switch terminal connected to one of the anode output terminal and the cathode output terminal, and
a resistor, connected in series with the switch and disposed outside of the high voltage tank, which receives an application of wave tail voltage to discharge the flow of charges accumulated as stray capacitance, the resistor including a first resistor terminal connected to the other one of the anode output terminal and the cathode output terminal.

* * * * *